(12) United States Patent
Sewell et al.

(10) Patent No.: US 9,046,754 B2
(45) Date of Patent: Jun. 2, 2015

(54) EUV MASK INSPECTION SYSTEM

(75) Inventors: Harry Sewell, Ridgefield, CT (US); Eric Brian Catey, Danbury, CT (US); Adel Joobeur, Milford, CT (US); Yevgeniy Konstantinovich Shmarev, Lagrangeville, NY (US)

(73) Assignee: ASML Holding N.V., Veldhoven (NL)

( * ) Notice: Subject to any disclaimer, the term of this patent is extended or adjusted under 35 U.S.C. 154(b) by 1116 days.

(21) Appl. No.: 12/605,627

(22) Filed: Oct. 26, 2009

(65) Prior Publication Data

US 2010/0149505 A1   Jun. 17, 2010

Related U.S. Application Data

(60) Provisional application No. 61/138,389, filed on Dec. 17, 2008.

(51) Int. Cl.
  G03B 27/52     (2006.01)
  G03B 27/54     (2006.01)
  (Continued)

(52) U.S. Cl.
  CPC ............ *G03B 27/54* (2013.01); *G03F 7/70275* (2013.01); *G03F 7/70208* (2013.01); *G03F 7/7085* (2013.01); *G03F 7/70991* (2013.01); *G01N 2021/95676* (2013.01)

(58) Field of Classification Search
  CPC .................... G01N 2021/95676; G01N 21/94; G01N 21/956; G03B 27/54; G03F 7/22; G03F 7/24; G03F 7/84; G03F 7/7091; G03F 7/70133; G03F 7/702; G03F 7/70208; G03F 7/70783; G03F 7/7085; G03F 7/70866; G03F 7/70908; G03F 7/70916; G03F 7/70983; G03F 7/70991
  USPC ........... 355/30, 45, 52, 53, 55, 67–71, 75, 77; 356/237.2–237.6, 239.1–239.8, 356/335–434, 487; 430/5, 8, 30, 311, 312; 250/492.1, 492.2, 492.22, 548

See application file for complete search history.

(56) References Cited

U.S. PATENT DOCUMENTS 4,633,504 A * 12/1986 Wihl .............................. 382/144
4,679,215 A   7/1987 Nielsen et al.
(Continued)

FOREIGN PATENT DOCUMENTS

JP   06-349715 A   12/1994
JP   2000-031021 A   1/2000
(Continued)

OTHER PUBLICATIONS

English language Abstract of Japanese Patent Publication No. 06-349715 A, published Dec. 22, 1994; 1 page.
(Continued)

*Primary Examiner* — Christina Riddle
(74) *Attorney, Agent, or Firm* — Sterne, Kessler, Goldstein & Fox P.L.L.C.

(57) ABSTRACT

Disclosed are apparatuses, methods, and lithographic systems for EUV mask inspection. An EUV mask inspection system can include an EUV illumination source, an optical system, and an image sensor. The EUV illumination source can be a standalone illumination system or integrated into the lithographic system, where the EUV illumination source can be configured to illuminate an EUV radiation beam onto a target portion of a mask. The optical system can be configured to receive at least a portion of a reflected EUV radiation beam from the target portion of the mask. Further, the image sensor can be configured to detect an aerial image corresponding to the portion of the reflected EUV radiation beam. The EUV mask inspection system can also include a data analysis device configured to analyze the aerial image for mask defects.

14 Claims, 9 Drawing Sheets

(51) Int. Cl.
  *G03B 27/62* (2006.01)
  *G03B 27/32* (2006.01)
  *G03F 7/20* (2006.01)
  G03B 13/26 (2006.01)
  G01N 21/956 (2006.01)

(56) References Cited

U.S. PATENT DOCUMENTS

| | | | |
|---|---|---|---|
| 4,805,123 A * | 2/1989 | Specht et al. | 382/144 |
| 4,822,748 A | 4/1989 | Janesick et al. | |
| 5,399,867 A | 3/1995 | Kohno | |
| 5,404,410 A | 4/1995 | Tojo et al. | |
| 5,548,401 A * | 8/1996 | Ozaki | 356/239.3 |
| 5,581,089 A * | 12/1996 | Kohno | 250/461.1 |
| 5,581,324 A | 12/1996 | Miyai et al. | |
| 5,818,576 A | 10/1998 | Morishige et al. | |
| 5,828,457 A * | 10/1998 | Tabata et al. | 356/394 |
| 6,268,093 B1 * | 7/2001 | Kenan et al. | 430/30 |
| 6,738,135 B1 * | 5/2004 | Underwood et al. | 356/237.5 |
| 6,900,888 B2 | 5/2005 | Yoshida et al. | |
| 6,963,395 B2 | 11/2005 | Goldberg | |
| 7,027,143 B1 * | 4/2006 | Stokowski et al. | 356/237.2 |
| 7,187,432 B2 | 3/2007 | Matsui | |
| 2002/0025479 A1 * | 2/2002 | Okamoto et al. | 430/5 |
| 2002/0051566 A1 | 5/2002 | Yamashita | |
| 2002/0058188 A1 | 5/2002 | Iwasaki et al. | |
| 2002/0186879 A1 * | 12/2002 | Hemar et al. | 382/149 |
| 2003/0016338 A1 | 1/2003 | Yasuda et al. | |
| 2003/0133087 A1 | 7/2003 | Shima | |
| 2003/0151002 A1 * | 8/2003 | Ito et al. | 250/492.1 |
| 2003/0197857 A1 * | 10/2003 | Yamashita | 356/237.2 |
| 2004/0188643 A1 * | 9/2004 | Weiss et al. | 250/559.42 |
| 2004/0225488 A1 | 11/2004 | Wang et al. | |
| 2005/0008944 A1 * | 1/2005 | Cerrina et al. | 430/5 |
| 2005/0052633 A1 * | 3/2005 | Mori et al. | 355/53 |
| 2005/0110987 A1 * | 5/2005 | Furman et al. | 356/237.4 |
| 2006/0054836 A1 * | 3/2006 | Tezuka et al. | 250/372 |
| 2007/0146695 A1 * | 6/2007 | Brouwer et al. | 356/237.4 |
| 2007/0260419 A1 * | 11/2007 | Hagiwara | 702/150 |
| 2010/0165310 A1 | 7/2010 | Sewell et al. | |

FOREIGN PATENT DOCUMENTS

| | | |
|---|---|---|
| JP | 2000-098590 A | 4/2000 |
| JP | 2002-169267 A | 6/2002 |

OTHER PUBLICATIONS

English language Abstract of Japanese Patent Publication No. 2000-031021 A, published Jan. 28, 2000; 1 page.
English language Abstract of Japanese Patent Publication No. 2000-098590 A, published Apr. 7, 2000; 1 page.
English language Abstract of Japanese Patent Publication No. 2002-169267 A, published Jun. 14, 2006; 1 page.
English language translation of Japanese Notice of Reasons for Rejection directed to related Japanese Patent Application No. 2009-279059, mailed Jul. 15, 2011 from The Japanese Patent Office; 3 pages.
Non-Final Rejection mailed May 31, 2012 for U.S. Appl. No. 12/582,825, filed Oct. 21, 2009; 25 pages.
Final Rejection mailed Oct. 1, 2012 for U.S. Appl. No. 12/582,825, filed Oct. 21, 2009; 29 pages.
Non-Final Rejection mailed Feb. 26, 2014 for U.S. Appl. No. 12/582,825, filed Oct. 21, 2009; 30 pages.
Final Rejection mailed May 22, 2014 for U.S. Appl. No. 12/582,825, filed Oct. 21, 2009; 28 pages.

* cited by examiner

EUV MASK INSPECTION SYSTEM

CROSS REFERENCE TO RELATED APPLICATIONS

This application claims benefit under 35 U.S.C. §119(e) to U.S. Provisional Patent Application No. 61/138,389, filed Dec. 17, 2008, which is incorporated by reference herein in its entirety.

FIELD

The present invention generally relates to lithography, and more particularly to mask inspection using an extreme ultraviolet (EUV) illumination source.

BACKGROUND

Lithography is widely recognized as a key process in manufacturing integrated circuits (ICs) as well as other devices and/or structures. A lithographic apparatus is a machine, used during lithography, which applies a desired pattern onto a substrate, such as onto a target portion of the substrate. During manufacture of ICs with a lithographic apparatus, a patterning device (which is alternatively referred to as a mask or a reticle) generates a circuit pattern to be formed on an individual layer in an IC. This pattern can be transferred onto the target portion (e.g., comprising part of, one, or several dies) on the substrate (e.g., a silicon wafer). Transfer of the pattern is typically via imaging onto a layer of radiation-sensitive material (e.g., resist) provided on the substrate. In general, a single substrate contains a network of adjacent target portions that are successively patterned. Manufacturing different layers of the IC often requires imaging different patterns on different layers with different reticles or masks.

As the dimensions of ICs decrease and the patterns being transferred from the mask to the substrate become more complex, defects in the features formed on the mask become increasingly important. Consequently, defects in the features formed on the mask translate into pattern defects formed on the substrate. Mask defects can come from a variety of sources such as, for example, defects in coatings on mask blanks, the mask patterning process in a mask shop, and mask handling and contamination defects in a wafer fabrication facility. Therefore, inspection of masks for defects is important to minimize or remove unwanted particles and contaminants from affecting the transfer of a mask pattern onto the substrate.

SUMMARY

Given the foregoing, what is needed is an improved mask inspection system to support the minimization or removal of defects from mask patterns transferred onto a substrate. To meet this need, embodiments of the present invention are directed to an extreme ultraviolet (EUV) mask inspection system.

Embodiments of the present invention include a mask inspection system. The mask inspection system includes an EUV illumination source configured to illuminate an EUV radiation beam onto a target portion of a mask, an optical system configured to receive at least a portion of a reflected EUV radiation beam from the target portion of the mask, and an image sensor configured to detect an aerial image corresponding to the portion of the reflected EUV radiation beam. The mask inspection system can also include an inspection stage configured to support the mask during a mask inspection mode and a wafer exposure mode of operation.

The EUV illumination source can include a diverter device configured to switch the EUV illumination source between a mask inspection mode and a wafer exposure mode of operation. Alternatively, the diverter device can be configured to simultaneously illuminate an EUV radiation beam onto a mask in a patterning device of a lithographic apparatus and onto a mask in a mask inspection device.

Further, the mask inspection system can include a data analysis device configured to analyze the aerial image for mask defects. The data analysis device can be configured to analyze the aerial image in one of three modes of operation: comparison of the aerial image to a previous aerial image detected by the mask inspection system; comparison of a first pattern area of the mask with a second pattern of the mask, where the first pattern are is substantially identical to the second pattern area; and, comparison of the aerial image to reference data stored in a design database.

Embodiments of the present invention additionally include a method to inspect a mask for defects. The method includes the following: illuminating an EUV radiation beam onto a target portion of the mask; receiving at least a portion of a reflected EUV radiation beam from the target portion of the mask; and, detecting an aerial image corresponding to the portion of the reflected EUV radiation beam. The method can also include analyzing the aerial image for mask defects.

Embodiments of the present invention further include a lithography system with two illumination systems, where a first illumination system can be used to pattern a substrate and the other illumination system can be used for mask defect inspection. The lithography system includes the following components: a first illumination system configured to condition a first EUV radiation beam; a support constructed to support a first patterning device, the first patterning device configured to impart the first EUV radiation beam with a pattern in its cross-section to form a patterned radiation beam; a substrate table constructed to hold a substrate; a projection system configured to focus the patterned radiation beam onto the substrate; and, a mask inspection system. The mask inspection system includes a second illumination system configured to illuminate a second EUV radiation beam onto a target portion of a second patterning device, an optical system configured to receive at least a portion of a reflected EUV radiation beam from the target portion of the second patterning device, and an image sensor configured to detect an aerial image corresponding to the portion of the reflected EUV radiation beam.

Embodiments of the present invention also include another lithography system with a single illumination system configured to be used to pattern a substrate and for mask defect inspection. The lithography system includes the following components: an illumination system configured to condition a first EUV radiation beam and to illuminate a second EUV radiation beam onto a target portion of a first patterning device; a support constructed to support a second patterning device, the second patterning device configured to impart the first EUV radiation beam with a pattern in its cross-section to form a patterned radiation beam; a substrate table constructed to hold a substrate; a projection system configured to focus the patterned radiation beam onto the substrate; and, a mask inspection system. The mask inspection system includes an optical system configured to receive at least a portion of a reflected EUV radiation beam from the target portion of the first patterning device and an image sensor configured to detect an aerial image corresponding to the portion of the reflected EUV radiation beam.

Further features and advantages of the invention, as well as the structure and operation of various embodiments of the present invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
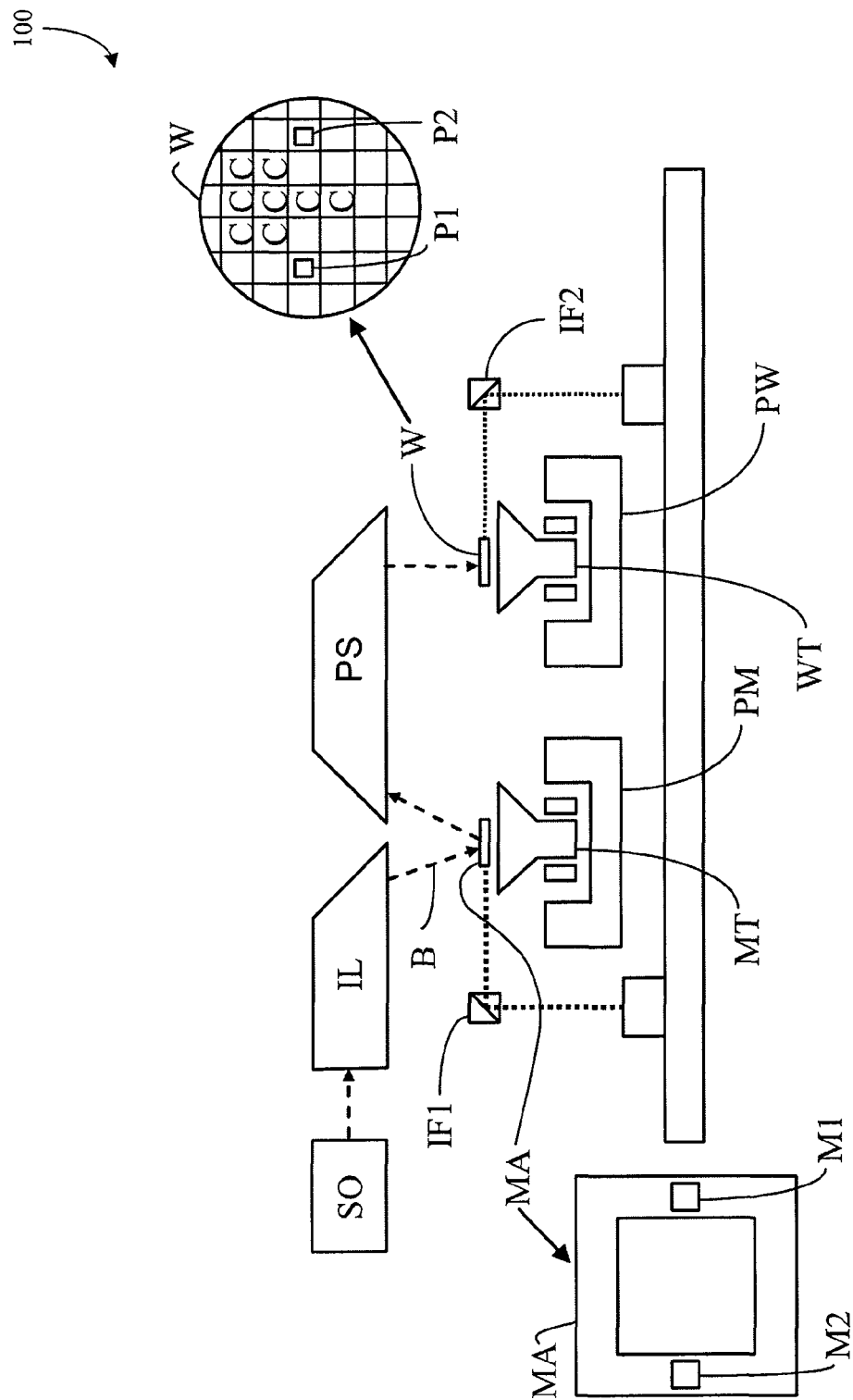
FIG. 1 is an illustration of an example reflective lithographic apparatus, in which embodiments of the present invention can be implemented.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Overview

Embodiments of the present invention are directed to an EUV mask inspection system. This specification discloses one or more embodiments that incorporate the features of the present invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention can be implemented in hardware, firmware, software, or any combination thereof. Embodiments of the present invention can also be implemented as instructions stored on a machine-readable medium, which can be read and executed by one or more processors. A machine-readable medium can include any mechanism for storing or transmitting information in a form readable by a machine (e.g., a computing device). For example, a machine-readable medium can include the following: read-only memory (ROM); random access memory (RAM); magnetic disk storage media; optical storage media; and, flash memory devices. Further, firmware, software, routines, instructions can be described herein as performing certain actions. However, it should be appreciated that such descriptions are merely for convenience and that such actions in fact result from computing devices, processors, controllers, or other devices executing the firmware, software, routines, instructions, etc.

Embodiments of the present inventions are directed to an EUV mask inspection system. The EUV mask inspection system can be used to measure an aerial image of features on a mask and identify potential mask defects. For instance, in a database comparison mode of operation, the EUV mask inspection system can be used by mask designers to obtain aerial images of a mask pattern as it would be used in a lithographic patterning process. These aerial images can be beneficial to mask design simulation tools to help accurately predict resulting features formed by a mask pattern (e.g., confirming the optical proximity corrections of the mask) and to optimize design of the mask.

Before describing such embodiments in more detail, however, it is instructive to present an example environment in which embodiments of the present invention can be implemented.

II. An Example Lithographic Environment

A. Example Reflective Lithographic System

FIG. 1 is an illustration of an example lithographic apparatus 100, in which embodiments of the present invention can be implemented. Lithographic apparatus 100 includes the following: an illumination system (illuminator) IL configured to condition a radiation beam B (e.g., EUV radiation, which has a wavelength less than 50 nm); a support structure (e.g., a mask table) MT configured to support a patterning device (e.g., a mask, a reticle, or a dynamic patterning device) MA and connected to a first positioner PM configured to accurately position the patterning device MA; and, a substrate table (e.g., a wafer table) WT configured to hold a substrate (e.g., a resist coated wafer) W and connected to a second positioner PW configured to accurately position the substrate W. Lithographic apparatuses 100 also has a projection system PS configured to project a pattern imparted to the radiation beam B by patterning device MA onto a target portion (e.g., comprising one or more dies) C of the substrate W. In lithographic apparatus 100, the patterning device MA and the projection system PS are reflective.

The illumination system IL can include various types of optical components, such as refractive, reflective, magnetic, electromagnetic, electrostatic or other types of optical components, or any combination thereof, for directing, shaping, or controlling the radiation B.

The support structure MT holds the patterning device MA in a manner that depends on the orientation of the patterning device MA, the design of lithographic 100, and other conditions, such as for example whether or not the patterning device MA is held in a vacuum environment. The support structure MT can use mechanical, vacuum, electrostatic, or other clamping techniques to hold the patterning device MA. The support structure MT can be a frame or a table, for example, which can be fixed or movable, as required. The support structure MT can ensure that the patterning device is at a desired position, for example, with respect to the projection system PS.

The term "patterning device" MA should be broadly interpreted as referring to any device that can be used to impart a radiation beam B with a pattern in its cross-section, such as to create a pattern in the target portion C of the substrate W. In reference to FIG. 1, pattern area PA contains one or more patterns to be transferred to the substrate W, where pattern areas PA can contain two or more substantially identical areas. The pattern imparted to the radiation beam B can correspond to a particular functional layer in a device being created in the target portion C, such as an integrated circuit.

The patterning device MA can be reflective (as in lithographic apparatus 100 of FIG. 1). Examples of patterning devices MA include reticles, masks, programmable mirror arrays, and programmable LCD panels. Masks are well known in lithography, and include mask types such as binary, alternating phase shift, and attenuated phase shift, as well as various hybrid mask types. An example of a programmable mirror array employs a matrix arrangement of small mirrors, each of which can be individually tilted so as to reflect an incoming radiation beam in different directions. The tilted mirrors impart a pattern in the radiation beam B which is reflected by the mirror matrix.

The term "projection system" PS can encompass any type of projection system, including refractive, reflective, catadioptric, magnetic, electromagnetic and electrostatic optical systems, or any combination thereof, as appropriate for the exposure radiation being used, or for other factors, such as the use of an immersion liquid or the use of a vacuum. A vacuum environment can be used for EUV or electron beam radiation since other gases can absorb too much radiation or electrons. A vacuum environment can therefore be provided to the whole beam path with the aid of a vacuum wall and vacuum pumps.

Lithographic apparatus 100 can be of a type having two (dual stage) or more substrate tables (and/or two or more mask tables) WT. In such "multiple stage" machines, the additional substrate tables WT can be used in parallel, or preparatory steps can be carried out on one or more tables while one or more other substrate tables WT are being used for exposure.

Referring to FIG. 1, the illuminator IL receives a radiation beam from a radiation source SO. The source SO and lithographic apparatus 100 can be separate entities, for example, when the source SO is an excimer laser. In such cases, the source SO is not considered to form part of lithographic apparatus 100, and the radiation beam B passes from the source SO to the illuminator IL with the aid of a beam delivery system BD (not shown in FIG. 1) including, for example, suitable directing mirrors and/or a beam expander. In other cases, the source SO can be an integral part of lithographic apparatus 100—for example when the source SO is a mercury lamp. The source SO and the illuminator IL, together with the beam delivery system BD, if required, can be referred to as a radiation system.

Referring to FIG. 1, the radiation beam B is incident on the patterning device (e.g., mask) MA, which is held on the support structure (e.g., mask table) MT, and is patterned by the patterning device MA. In lithographic apparatus 100, the radiation beam B is reflected from the patterning device (e.g., mask) MA. After being reflected from the patterning device (e.g., mask) MA, the radiation beam B passes through the projection system PS, which focuses the radiation beam B onto a target portion C of the substrate W. With the aid of the second positioner PW and position sensor IF2 (e.g., an interferometric device, linear encoder, or capacitive sensor), the substrate table WT can be moved accurately (e.g., so as to position different target portions C in the path of the radiation beam B). Similarly, the first positioner PM and another position sensor IF1 can be used to accurately position the patterning device (e.g., mask) MA with respect to the path of the radiation beam B. Patterning device (e.g., mask) MA and substrate W can be aligned using mask alignment marks M1, M2 and substrate alignment marks P1, P2.

In general, movement of the mask table MT can be realized with the aid of a long-stroke module (coarse positioning) and a short-stroke module (fine positioning), which form part of the first positioner PM. Similarly, movement of the substrate table WT can be realized using a long-stroke module and a short-stroke module, which form part of the second positioner PW. In the case of a stepper (as opposed to a scanner) the mask table MT can be connected to a short-stroke actuator only or can be fixed. Mask MA and substrate W can be aligned using mask alignment marks M1, M2 and substrate alignment marks P1, P2. Although the substrate alignment marks (as illustrated) occupy dedicated target portions, they can be located in spaces between target portions (known as scribe-lane alignment marks). Similarly, in situations in which more than one die is provided on the mask MA, the mask alignment marks can be located between the dies.

Lithographic apparatus 100 can be used in at least one of the following modes:

1. In step mode, the support structure (e.g., mask table) MT and the substrate table WT are kept essentially stationary, while an entire pattern imparted to the radiation beam B is projected onto a target portion C at one time (i.e., a single static exposure). The substrate table WT is then shifted in the X and/or Y direction so that a different target portion C can be exposed.

2. In scan mode, the support structure (e.g., mask table) MT and the substrate table WT are scanned synchronously while a pattern imparted to the radiation beam B is projected onto a target portion C (i.e., a single dynamic exposure). The velocity and direction of the substrate table WT relative to the support structure (e.g., mask table) MT can be determined by the (de-)magnification and image reversal characteristics of the projection system PS.

3. In another mode, the support structure (e.g., mask table) MT is kept substantially stationary holding a programmable patterning device, and the substrate table WT is moved or scanned while a pattern imparted to the radiation beam B is projected onto a target portion C. A pulsed radiation source SO can be employed and the programmable patterning device is updated as required after each movement of the substrate table WT or in between successive radiation pulses during a scan. This mode of operation can be readily applied to maskless lithography that utilizes a programmable patterning device, such as a programmable mirror array of a type as referred to herein.

Combinations and/or variations on the described modes of use or entirely different modes of use can also be employed.

Although specific reference can be made in this text to the use of lithographic apparatus in the manufacture of ICs, it should be understood that the lithographic apparatus described herein can have other applications, such as the manufacture of integrated optical systems, guidance and detection patterns for magnetic domain memories, flat-panel displays, liquid-crystal displays (LCDs), and thin-film magnetic heads. The skilled artisan will appreciate that, in the context of such alternative applications, any use of the terms "wafer" or "die" herein can be considered as synonymous with the more general terms "substrate" or "target portion," respectively. The substrate referred to herein can be processed, before or after exposure, in for example a track (a tool that typically applies a layer of resist to a substrate and develops the exposed resist), a metrology tool, and/or an inspection tool. Where applicable, the disclosure herein can be applied to such and other substrate processing tools. Further, the substrate can be processed more than once, for example, in order to create a multi-layer IC, so that the term substrate used herein can also refer to a substrate that already contains multiple processed layers.

In a further embodiment, lithographic apparatus 100 includes an extreme ultraviolet (EUV) source, which is configured to generate a beam of EUV radiation for EUV lithography. In general, the EUV source is configured in a radiation system (see below), and a corresponding illumination system is configured to condition the EUV radiation beam of the EUV source.

B. Example EUV Lithographic Apparatus

Figure 2:
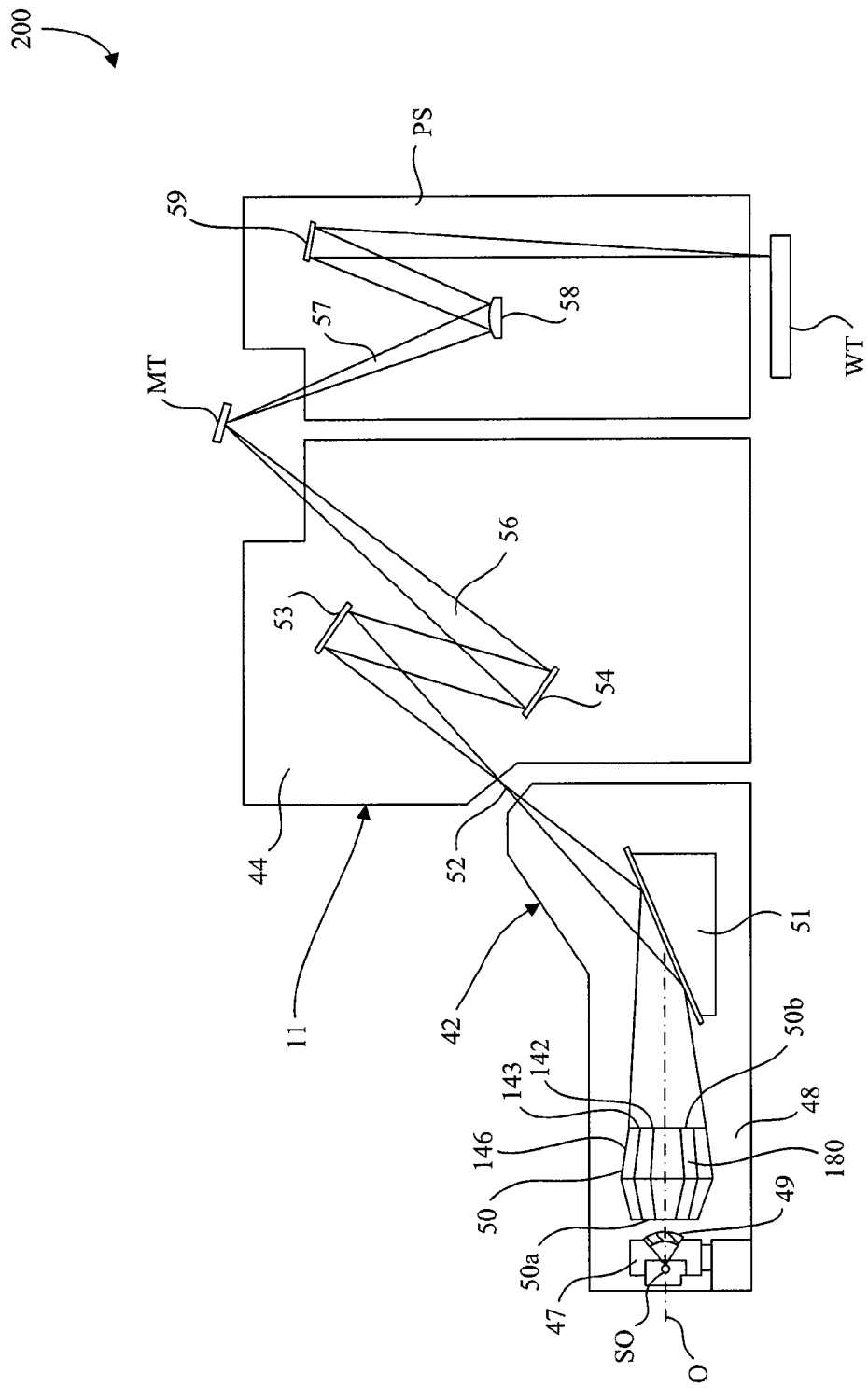
FIG. 2 is an illustration of an example EUV lithographic apparatus, in which embodiments of the present invention can be implemented.

FIG. 2 is an illustration of an example EUV lithographic apparatus 200, in which embodiments of the present invention can be implemented. In FIG. 2, EUV lithographic apparatus 200 includes a radiation system 42, an illumination optics unit 44, and a projection system PS. The radiation system 42 includes a radiation source SO, in which a beam of radiation can be formed by a discharge plasma. In an embodiment, EUV radiation can be produced by a gas or vapor, for example, from Xe gas, Li vapor, or Sn vapor, in which a very hot plasma is created to emit radiation in the EUV range of the electromagnetic spectrum. The very hot plasma can be created by generating at least partially-ionized plasma by, for example, an electrical discharge. Partial pressures of, for example, 10 Pa of Xe, Li, Sn vapor or any other suitable gas or vapor may be required for efficient generation of the radiation. The radiation emitted by radiation source SO is passed from a source chamber 47 into a collector chamber 48 via a gas barrier or contaminant trap 49 positioned in or behind an opening in source chamber 47. In an embodiment, gas barrier 49 can include a channel structure.

Collector chamber 48 includes a radiation collector 50 (which can also be called collector mirror or collector) that can be formed from a grazing incidence collector. Radiation collector 50 has an upstream radiation collector side 50a and a downstream radiation collector side 50b, and radiation passed by collector 50 can be reflected off a grating spectral filter 51 to be focused at a virtual source point 52 at an aperture in the collector chamber 48. Radiation collectors 50 are known to persons skilled in the relevant art(s).

From collector chamber 48, a beam of radiation 56 is reflected in illumination optics unit 44 via normal incidence reflectors 53 and 54 onto a mask (not shown) positioned on mask table MT. A patterned beam 57 is formed, which is imaged in projection system PS via reflective elements 58 and 59 onto a substrate (not shown) supported on wafer stage or substrate table WT. In various embodiments, illumination optics unit 44 and projection system PS can include more (or fewer) elements than depicted in FIG. 2. For example, grating spectral filter 51 can optionally be present, depending upon the type of lithographic apparatus. Further, in an embodiment, illumination optics unit 44 and projection system PS can include more mirrors than those depicted in FIG. 2. For example, projection system PS can incorporate one to four reflective elements in addition to reflective elements 58 and 59. In FIG. 2, reference number 180 indicates a space between two reflectors (e.g., space between reflectors 142 and 143).

In an embodiment, collector mirror 50 can also include a normal incidence collector in place of or in addition to a grazing incidence mirror. Further, collector mirror 50, although described in reference to a nested collector with reflectors 142, 143, and 146, is herein further used as example of a collector.

Further, instead of a grating 51, as schematically depicted in FIG. 2, a transmissive optical filter can also be applied. Optical filters transmissive for EUV, as well as optical filters less transmissive for or even substantially absorbing UV radiation, are known to persons skilled in the relevant art(s). Hence, the use of "grating spectral purity filter" is herein further indicated interchangeably as a "spectral purity filter," which includes gratings or transmissive filters. Although not depicted in FIG. 2, EUV transmissive optical filters can be included as additional optical elements, for example, configured upstream of collector mirror 50 or optical EUV transmissive filters in illumination unit 44 and/or projection system PS.

The terms "upstream" and "downstream," with respect to optical elements, indicate positions of one or more optical elements "optically upstream" and "optically downstream," respectively, of one or more additional optical elements. Following the light path that a beam of radiation traverses through lithographic apparatus 200, a first optical element closer to source SO than a second optical element is configured upstream of the second optical element; the second optical element is configured downstream of the first optical element. For example, collector mirror 50 is configured upstream of spectral filter 51, whereas optical element 53 is configured downstream of spectral filter 51.

All optical elements depicted in FIG. 2 (and additional optical elements not shown in the schematic drawing of this embodiment) can be vulnerable to deposition of contaminants produced by source SO, for example, Sn. Such may be the case for the radiation collector 50 and, if present, the spectral purity filter 51. Hence, a cleaning device may be employed to clean one or more of these optical elements, as well as a cleaning method can be applied to those optical elements, but also to normal incidence reflectors 53 and 54 and reflective elements 58 and 59 or other optical elements, for example additional mirrors, gratings, etc.

Radiation collector 50 can be a grazing incidence collector, and in such an embodiment, collector 50 is aligned along an optical axis O. The source SO, or an image thereof, can also be located along optical axis O. The radiation collector 50 can include reflectors 142, 143, and 146 (also known as a "shell" or a Wolter-type reflector including several Wolter-type reflectors). Reflectors 142, 143, and 146 can be nested and rotationally symmetric about optical axis O. In FIG. 2, an inner reflector is indicated by reference number 142, an intermediate reflector is indicated by reference number 143, and an outer reflector is indicated by reference number 146. The radiation collector 50 encloses a certain volume (i.e., a volume within the outer reflector(s) 146). Usually, the volume within outer reflector(s) 146 is circumferentially closed, although small openings can be present.

Reflectors 142, 143, and 146 can include surfaces of which at least a portion represents a reflective layer or a number of reflective layers. Hence, reflectors 142, 143, and 146 (or additional reflectors in the embodiments of radiation collectors having more than three reflectors or shells) are at least partly designed for reflecting and collecting EUV radiation from source SO, and at least part of reflectors 142, 143, and 146 may not be designed to reflect and collect EUV radiation. For example, at least part of the back side of the reflectors may not be designed to reflect and collect EUV radiation. On the surface of these reflective layers, there can be an additional cap layer for protection, or as optical filter, provided on at least part of the surface of the reflective layers.

The radiation collector 50 can be placed in the vicinity of the source SO or an image of the source SO. Each reflector 142, 143, and 146 can include at least two adjacent reflecting surfaces, where the reflecting surfaces further from the source SO are placed at smaller angles to the optical axis O than the reflecting surface that is closer to the source SO. In this way, a grazing incidence collector 50 is configured to generate a beam of (E)UV radiation propagating along the optical axis O. At least two reflectors can be placed substantially coaxially and extend substantially rotationally symmetric about the optical axis O. It should be appreciated that radiation collector 50 can have further features on the external surface of outer reflector 146 or further features around outer reflector 146 such as, for example, a protective holder and a heater.

In the embodiments described herein, the terms "lens" and "lens element," where the context allows, can refer to any one or combination of various types of optical components, including refractive, reflective, magnetic, electromagnetic, and electrostatic optical components.

Further, the terms "radiation" and "beam" used herein encompass all types of electromagnetic radiation, including ultraviolet (UV) radiation (e.g., having a wavelength λ, of 365, 248, 193, 157 or 126 nm), extreme ultraviolet (EUV) radiation (e.g., having a wavelength less than 50 nm such as, for example, 13.5 nm), or hard X-ray working at less than 5 nm, as well as particle beams, such as ion beams or electron beams. Generally, radiation having wavelengths between about 780-3000 nm (or larger) is considered IR radiation. UV refers to radiation with wavelengths of approximately 100-400 nm. Within lithography, the term "UV" also applies to the wavelengths that can be produced by a mercury discharge lamp: G-line 436 nm; H-line 405 nm; and/or, I-line 365 nm. Vacuum UV, or VUV (i.e., UV absorbed by air), refers to radiation having a wavelength of approximately 100-200 nm. Deep UV (DUV) generally refers to radiation having wavelengths ranging from 126 nm to 428 nm, and in an embodiment, an excimer laser can generate DUV radiation used within a lithographic apparatus. It should be appreciated that radiation having a wavelength in the range of, for example, 5-20 nm relates to radiation with a certain wavelength band, of which at least part is in the range of 5-20 nm.

III. Embodiments of an EUV Mask Inspection System

Figure 3:
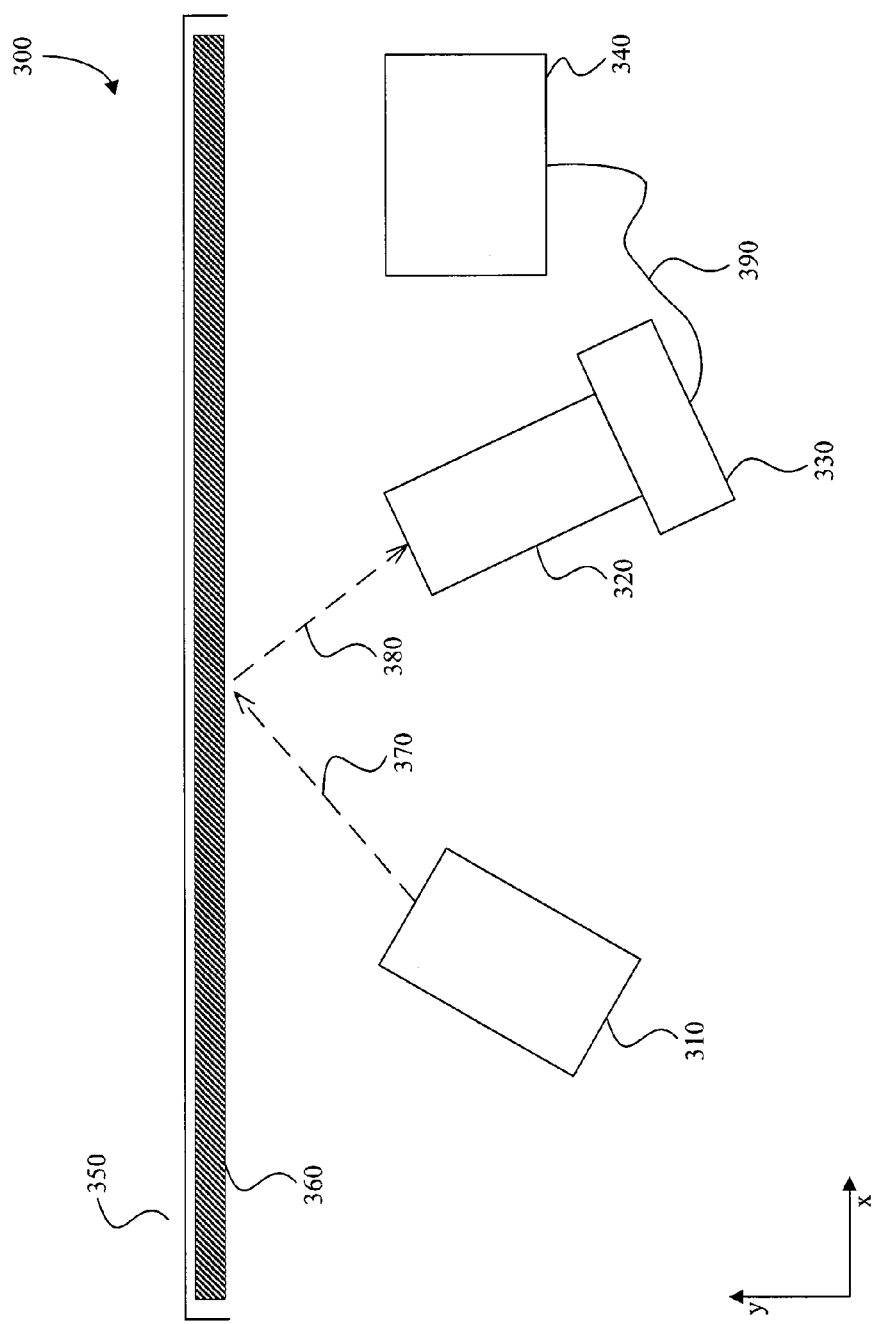
FIG. 3 is an illustration of an embodiment of an EUV mask inspection system.

FIG. 3 is an illustration of an embodiment of an EUV mask inspection system 300. EUV mask inspection system 300 includes an EUV illumination source 310, an optical system 320, an image sensor 330, a data analysis device 340, and an inspection stage 350. EUV illumination source 310 has a wavelength of less than 50 nm such as, for example, 13.5 nm. EUV mask inspection system resolves features on a mask 360 for the purposes of measuring an aerial image of features on mask 360 and identifying potential mask defects. For illustration purposes, the following description of EUV mask inspection system 300 will be in the context of a reflective patterning device (as in lithographic apparatus 100 of FIG. 1 and EUV lithographic apparatus 200 of FIG. 2).

Figure 4:
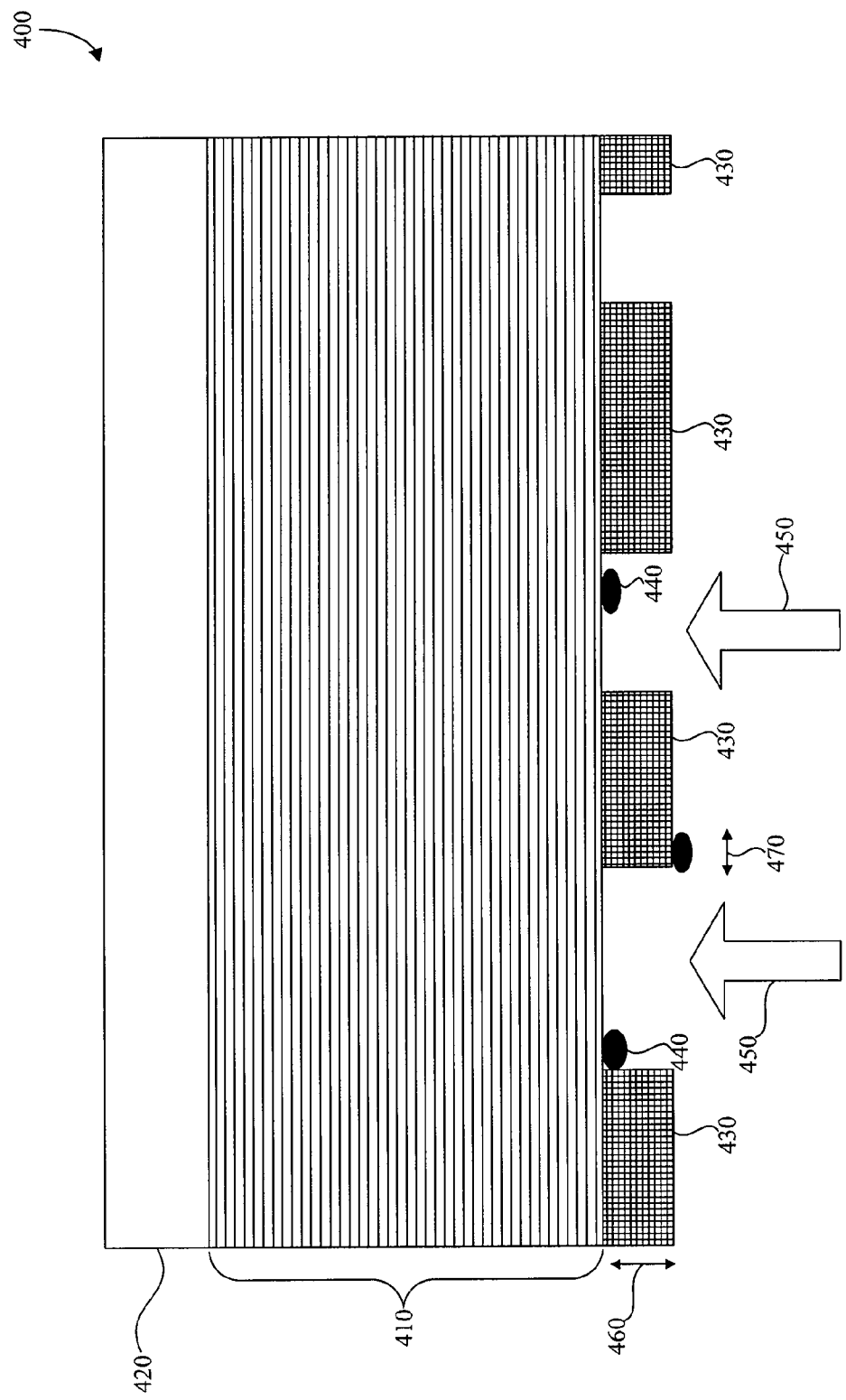
FIG. 4 is an illustration of an example mask used in a lithographic patterning process.

For explanation purposes, FIG. 4 is an illustration of an example mask 400 used in a lithographic patterning process. Mask 400 is composed of several layers of material 410, which form a Bragg reflector that enables mask 400 to reflect EUV radiation. Mask pattern 430 is a pattern to be transferred onto a surface of a substrate (not shown) via mask 400. Contaminants 440 can lie between or on mask pattern 430 and come from a variety of sources such as, for example, defects in coatings on mask blanks, the mask patterning process in a mask shop, and mask handling and contamination defects in a wafer fabrication facility, and the like. As an exposure of radiation 450 passes through mask 400, contaminants 440 can cause pattern defects to be formed on the substrate. It is therefore important to minimize or remove unwanted particles and contaminants from affecting the transfer of mask pattern 430 onto the substrate.

In a mask inspection tool operating based on scatterometry methods (e.g., light scatter defect inspection methods), light is typically illuminated onto a surface of the mask and an aerial image formed by light scattered from the surface of the mask is measured to detect defects in the mask pattern. The intensity of the light scattered by the defect is related to the wavelength of the illumination light and the size of the defect. As resolution of unwanted particles and contaminants decreases (e.g., a resolution less than 50 nm), mask inspection tools are faced with a challenge of detecting mask pattern defects at lower resolutions. For instance, in reference to FIG. 4, mask inspection tools that operate based on light scatter defect inspection methods at visible or near UV wavelengths can have difficulty differentiating between mask pattern 430 and mask pattern defect 440 when a feature size 460 of mask pattern 430 is much larger than a feature size 470 of defect 440. More specifically, light scatter from a larger mask pattern can easily drown out light scatter reflected off a smaller defect, which can result in the mask inspection tool failing to detect the mask defect.

Embodiments of the present invention can be used to improve the detection of defects in a mask inspection tool. In particular, in reference to FIG. 3, EUV illumination source 310 provides an EUV inspection beam 370 at an EUV wavelength range of, for example, less than 50 nm, thus improving the detection of defects at smaller resolutions. With EUV inspection beam 370, light scatter from a larger mask pattern (e.g., mask pattern 430 of FIG. 4) can be more easily resolved from light scatter reflected off smaller defects (e.g., defect 440 of FIG. 4), as compared to light scatter defect inspection methods using visible or near UV wavelengths. Embodiments of the present invention are directed to resolving mask defects with an EUV illumination source that provides an EUV inspection beam at wavelengths less than 50 nm.

EUV illumination source 310 is configured to project EUV inspection beam 370 onto a target portion of mask 360. An example of EUV illumination source 310 is radiation system 42 of FIG. 2. In an embodiment, the wavelength of EUV inspection beam 370 can be substantially identical to the wavelength of EUV radiation beam in a lithographic apparatus used to pattern a substrate. In using substantially identical wavelengths for EUV inspection beam 370 and the EUV radiation beam used to pattern the substrate, an aerial image of the mask pattern (as it would be used in a lithographic patterning process) can be obtained. The aerial image of the mask pattern may not only be used in a lithographic apparatus integrating EUV mask inspection system 300 but may also be used in applications outside of EUV mask inspection system 300. For instance, data from the aerial image can be used in mask design simulation tools to accurately predict resulting features formed by the mask pattern when exposed with a particular wavelength of EUV radiation beam (e.g., confirming the optical proximity corrections of the mask).

EUV illumination source 310 can be a standalone light source according to an embodiment of the present invention. In this embodiment, a lithographic apparatus integrating EUV mask inspection system 300 can be configured to operate in a mask inspection mode to analyze defects in a mask pattern (e.g., mask pattern 430 of FIG. 4) using the standalone light source and to also operate in a wafer exposure mode, where an alternate illumination source (e.g., illuminator IL in FIG. 1) is used when conditioning a radiation beam to transfer a mask pattern onto a substrate.

In another embodiment, EUV illumination source 310 is integrated into an illumination source used in a lithographic patterning process (e.g., illuminator IL in FIG. 1). In particular, EUV illumination source 310 can be used in both a mask inspection mode and a wafer exposure mode of operation. In an embodiment, during the wafer inspection mode, an EUV radiation beam can be taken from an intermediate focal point in the EUV illumination source (used in the lithographic patterning process), conditioned, and relayed to an area of inspection on the mask (e.g., portion of mask pattern 430 in FIG. 4). During the wafer inspection mode, an EUV radiation beam from the EUV illumination source can be conditioned and relayed onto a target portion of the mask, in which the EUV radiation beam reflects off the mask and is subsequently focused onto a target portion of the substrate via a projection system (e.g., projection system PS of FIG. 1).

Figure 5:
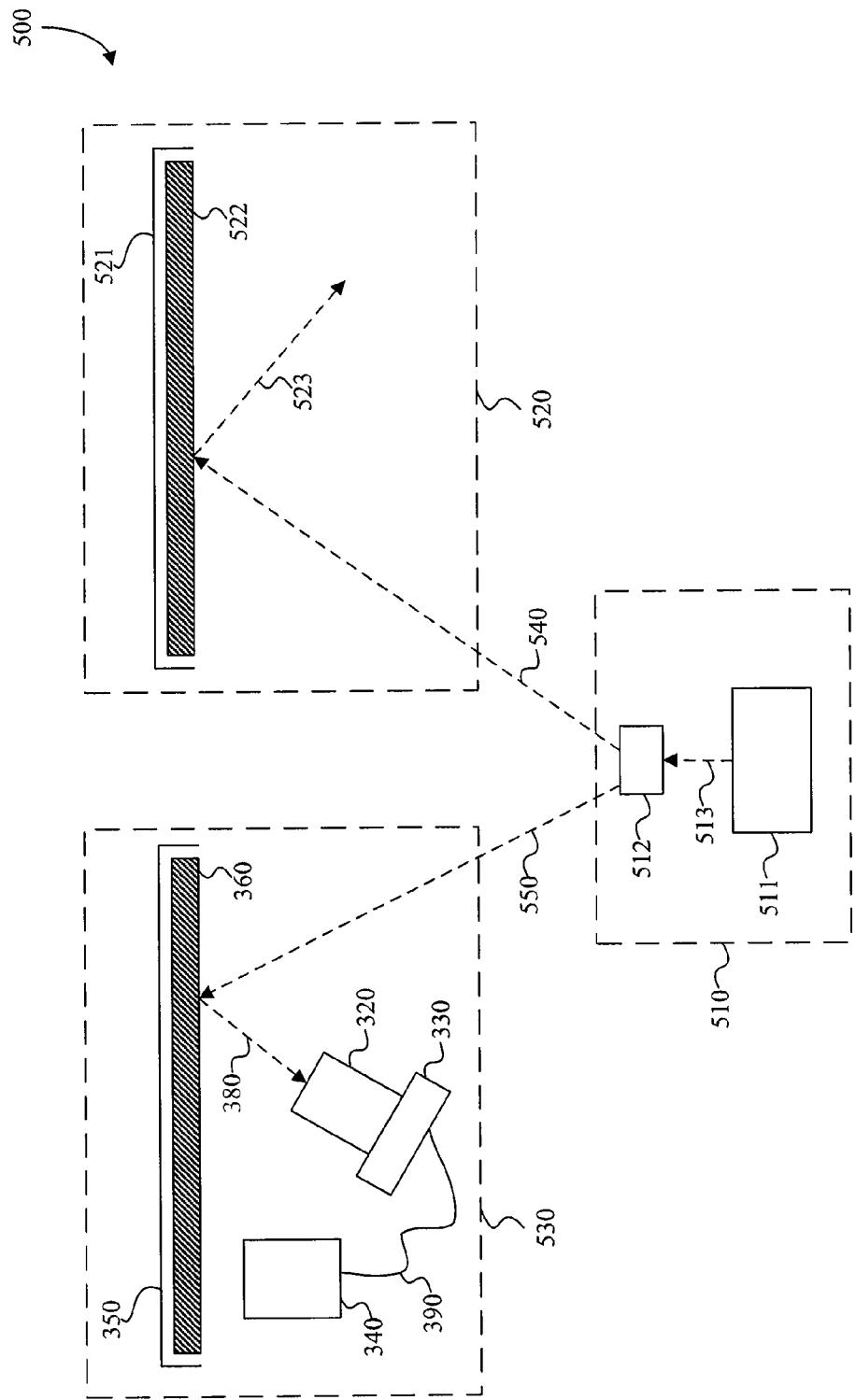
FIG. 5 is an illustration of an embodiment of a lithographic apparatus with an EUV illumination source used during a mask inspection mode and a wafer exposure mode of operation.

FIG. 5 is an illustration of an embodiment of a lithographic apparatus 500 with an EUV illumination source 510 used during a mask inspection mode and a wafer exposure mode of operation. Lithographic apparatus 500 includes an EUV illumination source 510, a wafer patterning device 520, and a mask inspection device 530. In an embodiment, mask inspection device 530 includes optical system 320, image sensor 330, data analysis device 340, and inspection stage 350. The components of mask inspection device 530 function in a similar manner as the components of EUV mask inspection system 300 of FIG. 3.

In an embodiment, wafer patterning device 520 includes a mask 522 and a mask table 521 to support mask 522. Wafer patterning device 520 is configured to receive an EUV radiation beam 540, where EUV radiation beam 540 reflects off a patterned surface on mask 522 and is further processed by a projection system (not shown) in lithographic apparatus 500. The projection system receives a reflected EUV radiation beam 523 and projects a pattern imparted on reflected EUV radiation beam 523 by mask 522 onto a target portion of a substrate (as in lithographic apparatus 100 of FIG. 1).

In an embodiment, EUV illumination source 510 includes an EUV light source 511 and a diverter device 512. EUV light source 511 is configured to direct an EUV radiation beam 513 to diverter device 512 and, in turn, diverter device 512 directs EUV radiation beam 540 to wafer patterning device 520 and an EUV radiation beam 550 to mask inspection device 530. In an embodiment, diverter device 512 includes a plurality of optical elements arranged to direct EUV radiation beam 513 to mask 522 (in wafer patterning device 520) and to mask 360 (in mask inspection device 530). Methods and optical element arrangements to direct a radiation beam, such as EUV radiation beam 513, to one or more directions are known to persons skilled in the relevant art(s). For instance, diverter device can be placed, for example, near virtual source point 52 of FIG. 2 to direct EUV radiation beam 513 to mask 522 and mask 360.

Diverter device 512 can be configured to simultaneously direct EUV radiation beam 513 to both mask 522 and mask 360 (via EUV radiation beam 540 and 550, respectively) according to an embodiment of the present invention. For instance, as a substrate receives a patterned EUV radiation beam (e.g., via reflected EUV radiation beam 523), mask 360 in mask inspection device 530 can be inspected for mask defects.

Figure 6:
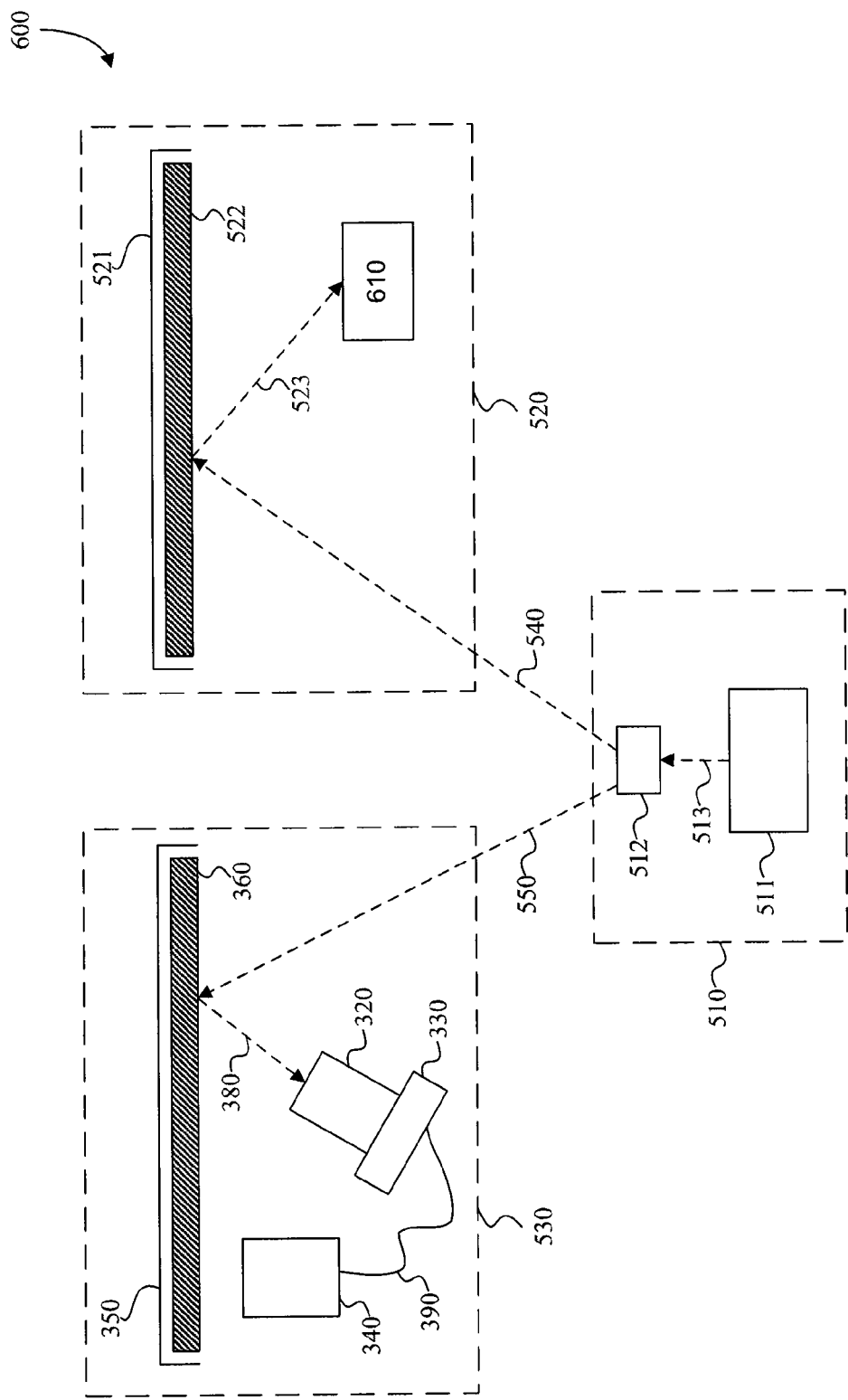
FIG. 6 is an illustration of another embodiment of a lithographic apparatus with an EUV illumination source used during a mask inspection mode and a wafer exposure mode of operation.

In another embodiment, diverter device 512 can be configured to simultaneously direct EUV radiation beam 522 to mask 360 and mask 522 for the inspection of defects in masks 522 and 360. For instance, FIG. 6 is an illustration of another embodiment of a lithographic apparatus 600 with EUV illumination source 510 used during the mask inspection mode and the wafer exposure mode of operation. FIG. 6 includes a mask inspection system 610, which operates in a similar manner as mask inspection system 300 of FIG. 3. In lithographic apparatus 600, mask inspection system 610 can be configured to receive reflected EUV radiation beam 523 and to inspect mask 522 for defects at the same time mask 360 is being inspected for defects. In an embodiment, mask 360 and mask 522 contain substantially similar patterns and as mask 360 and mask 522 are simultaneously inspected for defects, an aerial image of pattern features on mask 360 can be compared to a corresponding aerial image of pattern features on mask 522. The comparison of these aerial images from masks 360 and 522 can facilitate in the identification of defects (explained further below in pattern-to-pattern comparison mode of operation). In the alternative, mask inspection system 610 can be arranged or configured to bypass reflected EUV radiation beam 523 during the wafer exposure mode of operation, while mask 360 is being inspected for defects.

In reference to FIG. 5, diverter device 512 can be configured to direct EUV radiation beam 513 to either mask 522 or mask 360 depending on the mode of operation of lithographic apparatus 500 according to an embodiment of the present invention. That is, during a wafer exposure mode of operation, diverter device 512 directs EUV radiation beam 513 towards mask 522 in wafer patterning device 520, where reflected EUV radiation beam 523 is further processed by a projection system (not shown) and focused onto a target portion of a substrate (e.g., as described above with respect to FIG. 1).

Diverter device 512 also directs EUV radiation beam 513 towards mask 360 in mask inspection device 530 during a mask inspection mode of operation. For instance, between patterning two or more substrates with mask 522 in wafer patterning device 520, diverter device 512 can direct EUV radiation beam 513 towards mask 360 and inspect mask 360 for defects while an already-patterned substrate is replaced with a substrate that requires patterning. Here, diverter device 512 does not direct EUV radiation beam 540 towards mask 522 when the already-patterned substrate is being replaced by the substrate to be patterned. In another example, diverter device 512 can direct EUV radiation beam 513 towards mask 360 and inspect mask 360 for defects when EUV beam 540 reaches an edge of mask 522 (e.g., change in scan direction) during a rasterization exposure of mask 522. That is, as EUV radiation beam 540 increments to the next row or column of mask 522 to expose with EUV radiation beam 540, EUV illumination source 510 can divert EUV radiation beam 513 towards mask 360 for inspection of defects as wafer patterning device 520 prepares for the next row or column of mask 522 to be exposed onto the substrate.

In reference to FIG. 3, inspection stage 350 is configured to support mask 360 during a mask inspection mode of operation, according to an embodiment of the present invention. In an embodiment, inspection stage 350 is a standalone high-precision mask table (e.g., support table MT of FIG. 1) that is used during the mask inspection mode of operation, where the standalone high-precision mask table is configured to accurately position the mask in x- and y-directions (e.g., via interferometric devices, linear encoders, or capacitive sensors). In another embodiment, inspection stage 350 is a high-precision mask table that can be used during a mask inspection mode and a wafer exposure mode of operation. High-precision mask tables are known to persons skilled in the relevant art(s).

In yet another embodiment, inspection stage 350 is a standalone high-precision mask table that is integrated into a lithography system (e.g., lithographic apparatus 100 of FIG. 1). In this embodiment, inspection stage 350 can be located in a mask inspection system (e.g., EUV mask inspection system 300) that is in a separate compartment from a wafer patterning system. For instance, an exposure stage can be used during a wafer exposure mode of operation and inspection stage 350 can be used during a mask inspection mode of operation such that, after the wafer exposure and mask inspection modes of operation are complete, the mask supported by inspection stage 350 can be transferred to the exposure stage for subsequent lithographic processes.

Optical system 320 is configured to receive at least a portion of a reflected EUV radiation beam 380 from a target portion of mask 360, according to an embodiment of the present invention. Optical system 320 is configured to condition, magnify, and direct reflected EUV radiation beam 380 onto image sensor 330. In an embodiment, the magnification factor of reflected EUV radiation beam 380 onto image sensor 330 depends on the size of a detector array located in sensor array 330 (described further below). Methods and optical element arrangements to condition, magnify, and direct reflected EUV radiation beam 380 onto image sensor 330 are known to persons skilled in the relevant art(s).

Image sensor 330 is configured to detect an aerial image corresponding to a portion of reflected EUV radiation beam 380 received by optical system 320, according to an embodiment of the present invention. In an embodiment, image sensor 330 includes a detector array. An example of a detector array is a silicon charge-coupled device array of sensors. Based on the description herein, a person skilled in the relevant art(s) will recognize that other types of sensors and detectors can be used in image sensor 330. These other types of sensors and detectors are within the scope and spirit of the present invention.

Design of the detector array can depend on several factors such as, for example, physical size and detection resolution of the array. For instance, the detector array can consist of 24,000 by 24,000 sensor cells, where each sensor cell in 5 μm by 5 μm. This example detector array would be in the order of 100 mm by 100 mm. In order to resolve a mask defect (e.g., mask defect 440 of FIG. 4) with a feature size of 10 nm, reflected EUV radiation beam 380 received by optical system 320 would need to be magnified by at least 500 times in order for the detector array to resolve the defect. To resolve mask defects with a smaller feature size than 10 nm, adjustments can be made to either the magnification of optical system 320 or to the design of the detector array, or both, in order to detect the smaller mask defect. A person skilled in the relevant art(s) will recognize that other parameters in EUV mask inspection system 300 can also be adjusted to resolve mask defects with various feature sizes such as, for example, a pixel resolution of the mask (e.g., pixel resolution=[size of sensor cell]/[magnification of optical system]).

Figure 7:
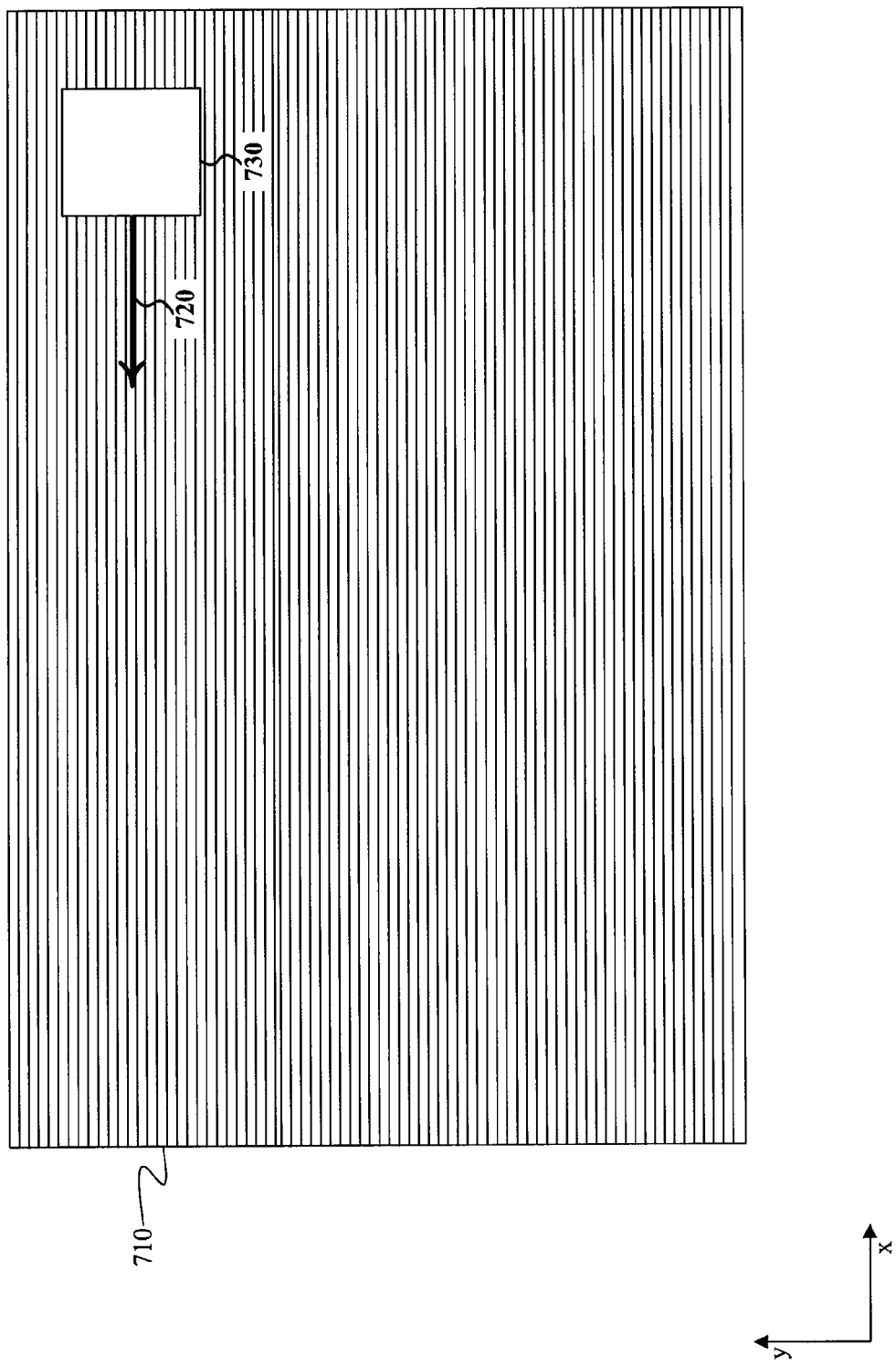
FIG. 7 is an illustration of an example mask illuminated with an EUV inspection beam from an EUV mask inspection system.

FIG. 7 is an illustration of an example mask 710 illuminated with an EUV inspection beam (e.g., EUV inspection beam 370 of FIG. 3) from an EUV mask inspection system. In an embodiment, image sensor 330 is configured to scan mask 610 in a scan direction 720 and record image data. An EUV illumination source (e.g., EUV illumination source 310 of FIG. 3) illuminates an area 730, where an EUV radiation beam reflected from area 730 (e.g., reflected EUV radiation beam 380 of FIG. 3) can be viewed using optical system 320 and detected by image sensor 330. In an embodiment, mask 710 can be scanned in a "raster-like" manner, where image sensor 330 scans mask 610 for image data along an x-direction (e.g., in a right-to-left direction) and advances downward in a y-direction (e.g., in a top-to-bottom direction) across mask 710 to scan for image data along the x-direction (e.g., in a left-to-right direction). Each scan line can be recorded by image sensor 330 or further processed into discrete pixels for processing by data analysis device 340. In the alternative, each scan line can be recorded by data analysis device 340. The culmination of the scan lines recorded by either image sensor 330 or data analysis device 340 form an aerial image of a pattern on mask 710.

Figure 8:
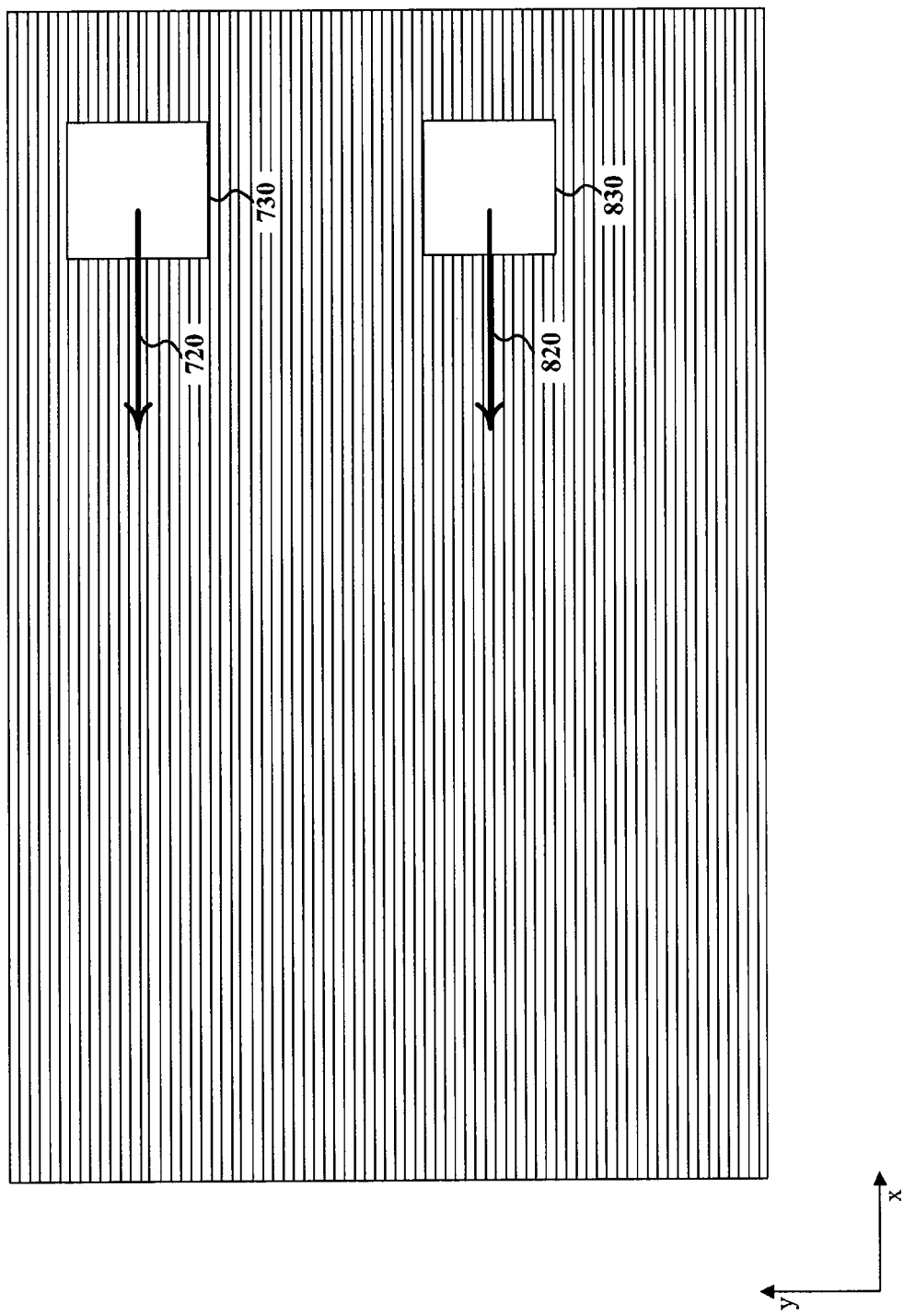
FIG. 8 is an illustration of an example mask illuminated with a plurality of EUV inspection beams from an EUV mask inspection system.

FIG. 8 is an illustration of example mask 710 illuminated with a plurality of EUV inspection beams from an EUV mask inspection system. In FIG. 8, a plurality of inspection areas 730 and 830 are analyzed. In an embodiment, areas 730 and 830 can be analyzed in parallel and in directions 720 and 820, where inspection area 730 can be used to scan across an upper portion of mask 710 and inspection area 830 can be used to scan across a bottom portion of mask 710. Each inspection area 730 and 830 has an EUV inspection beam directed towards it and an associated optical system and image sensor to detect an aerial image corresponding to each inspection area. In an embodiment, the EUV inspection beam directed towards inspection areas 730 and 830 can be derived from a single EUV illumination source with the use of, for example, a diverter device (e.g., diverter device 512 of FIG. 6).

In another embodiment, inspection areas 730 and 830 can analyze patterns on mask 710 with substantially similar features. For instance, an upper portion of mask 710 can contain a pattern that is substantially similar to a pattern located in a lower portion of mask 710. An aerial image of the pattern in the upper portion of mask 710 can be compared to a corresponding aerial image of the substantially similar pattern in the lower portion of mask 710 to highlight potential defects (explained further below in pattern-to-pattern comparison mode of operation). Based on the description herein, a person skilled in the art will recognize that more than two inspection areas can be analyzed (e.g., in parallel) on mask 710.

In reference to FIG. 3, data analysis device 340 is configured to analyze an aerial image detected by image sensor 330. Data corresponding to the aerial image detected by image sensor 330 is transferred from image sensor 330 to data analysis device 340 via data connection 390. In an embodiment, data connection 390 is configured to facilitate a high-speed data pipe between image sensor 330 and data analysis device 340. For instance, two or more optical fibers can be bundled together to provide a high-speed, parallel data transfer between image sensor 330 and data analysis device 340. Based on the description herein, a person skilled in the relevant art(s) will recognize that other types of data connections can be used to facilitate the data transfer between image sensor 330 and data analysis device 340.

In an embodiment, data analysis device 340 is configured to analyze the aerial image from image sensor 330 according to the following modes of operation: (1) mask image comparison; (2) pattern-to-pattern comparison; and, (3) database comparison. The mask image comparison mode of operation scans and records image data of a mask at two or more different points in time. Here, data analysis device 340 is configured to compute an aerial image corresponding to the recorded image data, compare a current aerial image with a previous aerial image of the mask, and highlight any differences between the aerial images as a potential mask defect.

In the pattern-to-pattern comparison mode of operation, a first pattern area of a mask is compared to a second pattern area of the mask, where the first pattern area and the second pattern area are designed to be substantially identical to one another. Here, data analysis device 340 is configured to compute an aerial image corresponding to the first and second pattern areas of the mask, compare the aerial image of the first pattern area with the aerial image of the second pattern area, and highlight any differences between the aerial images as a potential mask defect. In an embodiment, data analysis device 340 can be configured to compare one or more features of the first pattern area with one or more corresponding features of the second pattern area of the mask.

The database comparison mode of operation scans and records image data of a mask. Here, data analysis device 340 is configured to compute an aerial image corresponding to the recorded image data, compare the aerial image to a reference aerial image stored in a design database, and highlight any difference between the aerial images as a potential mask defect. In an embodiment, the design database can include image data corresponding to a calculated or previously-measured aerial image of the mask. The design database can be located within EUV mask inspection system 300 (e.g., within data analysis device 340) or external to EUV mask inspection system 300 (e.g., a standalone computing system).

Figure 9:
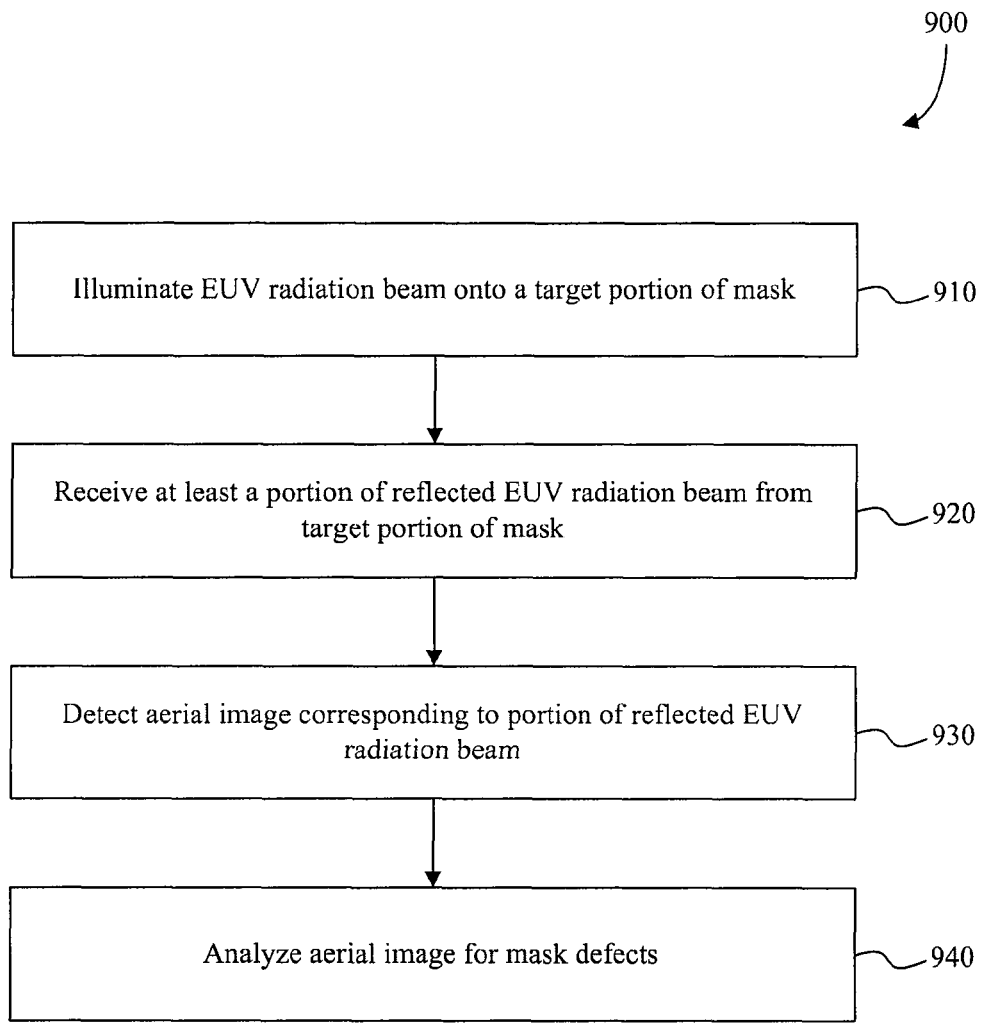
FIG. 9 is an illustration of an embodiment of a method for inspecting a mask for defects.

FIG. 9 is an illustration of an embodiment of a method 900 for inspecting a mask for defects. Method 900 can occur using, for example, EUV mask inspection system 300 described above with respect to FIG. 3. In step 910, a target portion of the mask is illuminated with an EUV radiation beam. In an embodiment, the EUV radiation beam is switched between a mask inspection mode and a wafer exposure mode of operation. For instance, when an EUV illumination source (e.g., EUV illumination source 310 of FIG. 3) is not being used during a wafer exposure mode of operation, the EUV illumination source can be used to inspect mask defects. Examples of instances when the EUV illumination source would not be used during the wafer mode of operation include an increment of row or column during a rasterization exposure of the mask (e.g., change in scan direction) and a replacement of an already-patterned wafer with a wafer that needs to be patterned.

In an embodiment, during these exemplary instances of when the wafer is not exposed to the patterned radiation beam, an entire mask or portions of a mask can be inspected for defects. The portions of the mask that are inspected in a "piece-meal" manner every time the lithographic apparatus switches between the mask inspection mode and the wafer exposure mode of operation can be combined to construct an overall aerial image of the mask.

In another embodiment, the EUV radiation beam simultaneously illuminates an EUV radiation beam onto a mask in a patterning device of a lithographic apparatus and onto a mask in a mask inspection device. EUV illumination source 510 of FIG. 5 can be used, for example, to illuminate the target portion of the mask with an EUV radiation beam.

In step 920, a portion (or the entire portion) of a reflected EUV radiation beam from the target portion of the mask is received by an optical system. The reflected EUV radiation beam can be received by, for example, optical system 320 of FIG. 3.

In step 930, an aerial image corresponding to the portion of the reflected EUV radiation beam (from step 920) is detected by an image sensor. Image sensor 330 of FIG. 3 can be used, for example, to detect the aerial image.

In step 940, the aerial image is analyzed for mask defects with a data analysis device. When analyzing the aerial image for mask defects, image data from the image sensor (from step 930) can be transferred to the data analysis device via a high-speed data connection such as, for example, a fiber optic-based data connection.

In an embodiment, the aerial image can be analyzed in one of three ways. First, the aerial image can be analyzed by comparing the aerial image to a previously detected aerial image. Second, the aerial image can be analyzed by comparing a first pattern of the mask with a second pattern area of the mask, where the first and second patterns are substantially identical to each other. Third, the aerial image can be compared to reference data stored in a design database.

IV. Conclusion

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:
1. A mask inspection system comprising:
an extreme ultraviolet (EUV) light source configured to direct an EUV radiation beam to a diverter device;
the diverter device configured to direct the EUV radiation beam onto a target portion of a first mask being used only in the mask inspection device and substantially simulta- neously direct the EUV radiation beam onto a second mask being used only in a wafer patterning device of a lithographic apparatus;
an optical system configured to receive at least a portion of a reflected EUV radiation beam from the of target portion of the first mask;
an image sensor configured to detect an aerial image corresponding to the portion of the reflected EUV radiation beam; and
a data analysis device configured to analyze the aerial image for mask defects.

2. The mask inspection system of claim 1, wherein the data analysis device is further configured to analyze the aerial images by at least one of:
comparing the aerial image to a previous aerial image detected by the mask inspection system;
comparing a first pattern area of the first mask with a second pattern area of the first mask, wherein the first pattern area is substantially identical to the second pattern area; and
comparing the aerial image to reference data stored in a design database.

3. The mask inspection system of claim 1, further comprising an inspection stage configured to support the first mask during a mask inspection mode and a wafer exposure mode of operation.

4. The mask inspection system of claim 1, wherein the image sensor comprises a silicon charge coupled device array of sensors.

5. The mask inspection system of claim 1, wherein the data analysis device is configured to analyze the aerial image for the mask defects by comparing in parallel a plurality of pattern areas with each other.

6. A method, comprising:
illuminating an extreme ultraviolet (EUV) radiation beam onto a target portion of a mask being used only in a mask inspection device;
substantially simultaneously illuminating the EUV radiation beam onto a second mask being used only in a wafer patterning device of a lithographic apparatus;
receiving at least a portion of a reflected EUV radiation beam from the target portion of the first mask;
detecting an aerial image corresponding to the portion of the reflected EUV radiation beam; and
analyzing the aerial image for mask defects.

7. The method of claim 6, wherein analyzing the aerial image further comprises at least one of:
comparing the aerial image to a previous aerial image detected by the mask inspection system;
comparing a first pattern area of the first mask with a second pattern area of the first mask, wherein the first pattern area is substantially identical to the second pattern area; and
comparing the aerial image to reference data stored in a design database.

8. The method of claim 6, wherein analyzing the aerial image comprises transferring data from an image sensor to a data analysis device.

9. The method of claim 6, further comprising supporting the first mask during an inspection mode and a wafer exposure mode of operation.

10. The method of claim 6, further comprising wherein the analyzing the aerial image for the mask defects further comprises:
comparing in parallel a plurality of pattern areas with each other.

11. A system, comprising:
an extreme ultraviolet (EUV) light source configured to direct an EUV radiation beam to a diverter device;
the diverter device configured to switch between directing the EUV radiation beam onto a target portion of a first patterning device in a mask inspection device and directing the EUV radiation beam onto a second patterning device in a wafer patterning device of a lithographic apparatus;
an optical system configured to receive at least a portion of a reflected EUV radiation beam from the target portion of the first patterning device;
an image sensor configured to detect an aerial image corresponding to the portion of the reflected EUV radiation beam; and
a data analysis device configured to analyze the aerial image for mask defects.

12. A lithography system, comprising:
an extreme ultraviolet (EUV) light source configured to direct an extreme ultraviolet (EUV) radiation beam to a diverter;
the diverter device configured to switch between directing the EUV radiation beam onto a target portion of a first patterning device in a mask inspection device and directing the EUV radiation beam onto a second patterning device in a wafer patterning device of a lithographic apparatus;
a support constructed to support the second patterning device, the second patterning device configured to impart the EUV radiation beam with a pattern in its cross-section to form a patterned radiation beam;
a substrate table constructed to hold a substrate;
a projection system configured to focus the patterned radiation beam onto the substrate; and
the mask inspection system comprising,
an optical system configured to receive at least a portion of a reflected EUV radiation beam from the target portion of the first patterning device,
an image sensor configured to detect an aerial image corresponding to the portion of the reflected EUV radiation beam, and
a data analysis device configured to analyze the aerial image for mask defects.

13. The lithography system of claim 12, wherein the diverter device is configured to direct the EUV radiation beam onto the target portion of the first patterning device, while at least one of the substrate is being replaced with a second substrate that requires patterning and a change in scan direction is required when patterning the substrate with the first EUV radiation beam.

14. The lithography system of claim 12, wherein:
the mask inspection system further comprises a second support constructed to support the first patterning device; and
the lithography system is configured to transfer the first patterning device to the support constructed to support the second patterning device such that the first patterning device is used as part of a lithographic patterning process.

* * * * *